US00PP09110P

United States Patent [19]

Klemm

[11] Patent Number: Plant 9,110

[45] Date of Patent: Apr. 18, 1995

[54] GERANIUM NAMED KLEGANY

[75] Inventor: Siegfried Klemm, Stuttgart, Germany

[73] Assignee: Klemm & Sohn, Stuttgart-Muhlhausen, Germany

[21] Appl. No.: 173,413

[22] Filed: Dec. 23, 1993

[51] Int. Cl.[6] ..... A01H 5/00

[52] U.S. Cl. ..... Plt./87.12

[58] Field of Search ..... Plt. 87.12

*Primary Examiner*—James R. Feyrer

*Attorney, Agent, or Firm*—Tilton, Fallon, Lungmus & Chestnut

[57] ABSTRACT

A new geranium cultivar particularly distinguished by its light purple flowers with a red center. The plant itself is strong with very compact branching, growing to a height of 280 mm.

1 Drawing Sheet

BACKGROUND OF THE NEW PLANT

The present invention comprises a new and distinct cultivar of geranium, botanically known as *Pelargonium zonale*—Hybride. The new cultivar is propagated from cuttings resulting from the cross of a pink purple seed parent with a red center derived from one of our breeding lines known as PAC Dresdner Puppe rosa mit Auge from our PAC variety and a pollen parent from our own breeding lines known as SEL "Klecerol" (U.S. Plant Pat. No. 7,410). PAC Dresdner Puppe rosa mit Auge has been available for many years by PAC Dresden. SEL "Klecerol" is pink with a white center. SEL "Klecerol" is commercially available. Klegany has large light purple flowers with a big red spot on broad petals. Klegany has a phenotype similar to that of Klegrand (U.S. Ser. No. 08/173,413). Klegany differs from Klegrand in that Klegany has fewer petals and/or petaloids, more elongated petal claws, is slightly higher but as compact and has less imbricated petals than Klegrand. Also, Klegany and Klegrand differ in their petal color and zonation. The petals of Klegany are purple-pink in color and the petals of Klegrand are more bluish in color. Also, the leaves of Klegany have no zonation.

This new plant is a product of a planned breeding program intended to create new geranium cultivars with light purple flowers having a big red spot on the petals, with vigorous growth and superior cutting productivity.

The new cultivar was bred in 1988, created in 1989, and selected in 1989, in Stuttgart, Germany and has been repeatedly asexually reproduced by cuttings in Stuttgart, Germany and Teneriffe, Itlay over a four year period. It has been found to retain its distinctive characteristics through successive propagations; and this novelty appears to be firmly fixed.

DESCRIPTION OF THE DRAWING

This new geranium plant is illustrated by the accompanying photographic drawing which shows blooms, buds, and foliage of the plant in full color, the color shown being as true as can be reasonably obtained by conventional photographic procedures.

DESCRIPTION OF THE NEW CULTIVAR

The following detailed description set forth the distinctive characteristics of this new geranium. The data which defines these characteristics was collected from asexuual reproductions carried out in Stuttgart, Germany. The plant history was taken on 10-week old plants, blossomed under natural light in a greenhouse. Color readings were taken in the greenhouse under ambient light. Color references are primarily to the R.H.S. Color Chart of The Royal Horticultural Society of London.

THE PLANT

Classification:

*Botanical.*—*Pelargonium zonale*—*Hybride.*

*Commercial.*—Zonal geranium.

Parentage:

*Seed parent.*—PAC Dresdner Puppe rosa mit Auge has pink purple flowers with a red spot. The precocity is early and the floral richness is very good. When this variety was bred, it was the first of all geraniums that had an eye or spot on the petals. But the flower was simple and had only five petals so that is shattered very easily. The foliage of Dresdner puppe rosa mit Auge was rather soft and the plant was not very compact and strong because of the time of vegetative growth was short in the spring.

*Pollen parent.*—"Klecerol" (U.S. Plant Pat. No. 7,410) is pink with a white center. The precocity is early to medium, producing small to medium sized flowers of 250–279 mm in height in September. "Klecerol" grows very compactly and branches very well. The large clusters with very many florets and buds stand on about 180mm long, strong stalks. The foliage is medium green, slightly zonated and robust.

Form: Bushy.

Shape; Very compact.

Height: 260–280 mm (in September).

Stem length: 150–200 mm in June and 260–280 mm in September.

Internode length: Very Short—5–8 mm.

Growth rate: For propagation begun in January, Klegany was marketable without pinching or Cyocel treatment in the middle of April depending on the weather.

Strength: Very good cutting producer for propagation, and the plant performs very well after shipping as a rooted or unrooted cutting.

Foliage:

*Leaves.*—Abundant quantity.

*Size.*—60 mm×70 mm to 65 mm to 80 mm.

*Shape.*—Kidney shaped.
*Margin.*—Crenate.
*Texture.*—Smooth.
Ribs and veins: None.
Zonation: None.
Color:
*Upper side.*—Green RHS 146-A.
*Under side.*—Green RHS 146-B.
Petioles of florets: About 25 mm.
Cluster stem: 100–130 mm.

THE BUD

Size:
*Diameter.*—About 8 mm.
*Length.*—About 10 mm at the time of bud opening.
Shape; Ovoid.
Color: Of petals when sepals first divide, you see the reverse side. The color of the reverse side is RHS 58-C. When the petals begin to unfurl, you see the inside of the petal. The inside petal is 57-C.
Sepals:
*Number.*—5.
*Shape.*—Pointed.
*Color.*—Inside — RHS 146-B. Outside — RHS 146-A.
*Length.*—Length: 25 mm. Strength: Erect and arranged hemispherically around the end of the cluster stalk. Color: RHS 187-C.

THE FLOWER

Blooming habit: Continuous throughout the year, until frost destroys plants.
Size: Approximately 50 mm in diameter, 10 mm deep.
Borne: Cluster.
Form: Cup-shaped when bloom first opens, later flattening to shallow cup shape with maturity.
Petals: Six to seven imbricate outer petals, 21 mm wide and approximately 24 mm long. There are one to two inner smaller petaloids. Both the outer petals and inner petals are pink — RHS 68-A. The outer petal is fuschia purple — RHS 67-A with a white spot at the base. On the inside petal the base is light purple — RHS 63-C with a spot of red — RHS 46-B. The under side of the petalsis lighter in color, RHS 68
*Pattern.*—Substantially the top, two mature petals of each floret variably express a pattern which includes a dark, red, blush-like spot in the central portion of the petal which effuses or bleeds, progressively, into the predominant purple-pink color (RHS 68A) of the top surface toward the margin. The spots are separated from the attachment points of these petals by a generally white, basal zone of substantially white color, except of the veins, which have the same color as the spot and form striations communicating the spot to the petal attachment points. The other petals, except the two upper petals with the big spots and the white basal zone, have smaller red spots and a light pink basal zone. These markings are not usually obscured by the much smaller, overlying petaloids do not express any spots. From a distance, the individual florets of this plant appear to have unusual star patter central to the flouret.
Petaloids:
*Number.*—One to two.
*Size.*—Very small 4–5 mm.
*Color.*—Pink — RHS 68-A.
Cluster stem:
*Length.*—100–130 mm.
*Color.*—Green — RHS 146-B.
*Characteristics.*—Sturdy and upright.
Pedicel: Approximately 23 mm in length.
Persistence: It is better to pick off the clusters that have only old and matured florets.
Disease resistance: The strong thick leaves do not suffer from Botrytis.
Weather resistance: Klegany is resistant to weather.
Lasting quality:
*On the plant.*—If you pick off old florets the cluster can stay for about 28 days.
*As a cut flower.*—About 6 days.
Fragrance: No perceptible fragrance.

INFLORESCENCE

Type: An umbel having between about 40–45 florets per cluster.
*Diameter.*—110 mm×70 mm.
*Borne.*—Very upright on strong green stems.
Blooming habit: It is not necessary to pinch the withered umbels because new buds are always appearing. It takes 19–28 days until one cluster is completely matured and becomes dry. Klegany had 307 cluster on 3 plants in 1990, 335 clusters on 3 plants in 1991 and 436 clusters on 3 plants in 1992.
Peduncle: Approximately 100–130 mm in length. Green in color.

REPRODUCTIVE ORGANS

Stamens:
*Anthers.*—Seven positioned around the ovaries with 2 mm length.
*Filaments.*—5–6 m in length and very light pink color.
*Pollen.*—Orange in color.
Pistil:
*Number.*—One.
*Length.*—Approximately 9 mm.
*Stigma.*—Purplish-pink in color.
Styles:
*Length.*—About 9 mm.
*Color.*—Dark pink and green
Ovaries: Green
Fruit: Fertile.
*Shape.*—Ovoid.
Length: About 3–4 mm long.
*Color at maturity.*—Brown.

I claim:

1. A new and distinct geranium cultivar substantially as herein shown and described, particularly distinguished by its light purple flowers with a red spot on broad petals, said cultivar being strong with very compact branching, growing to a height of 260–280 mm.

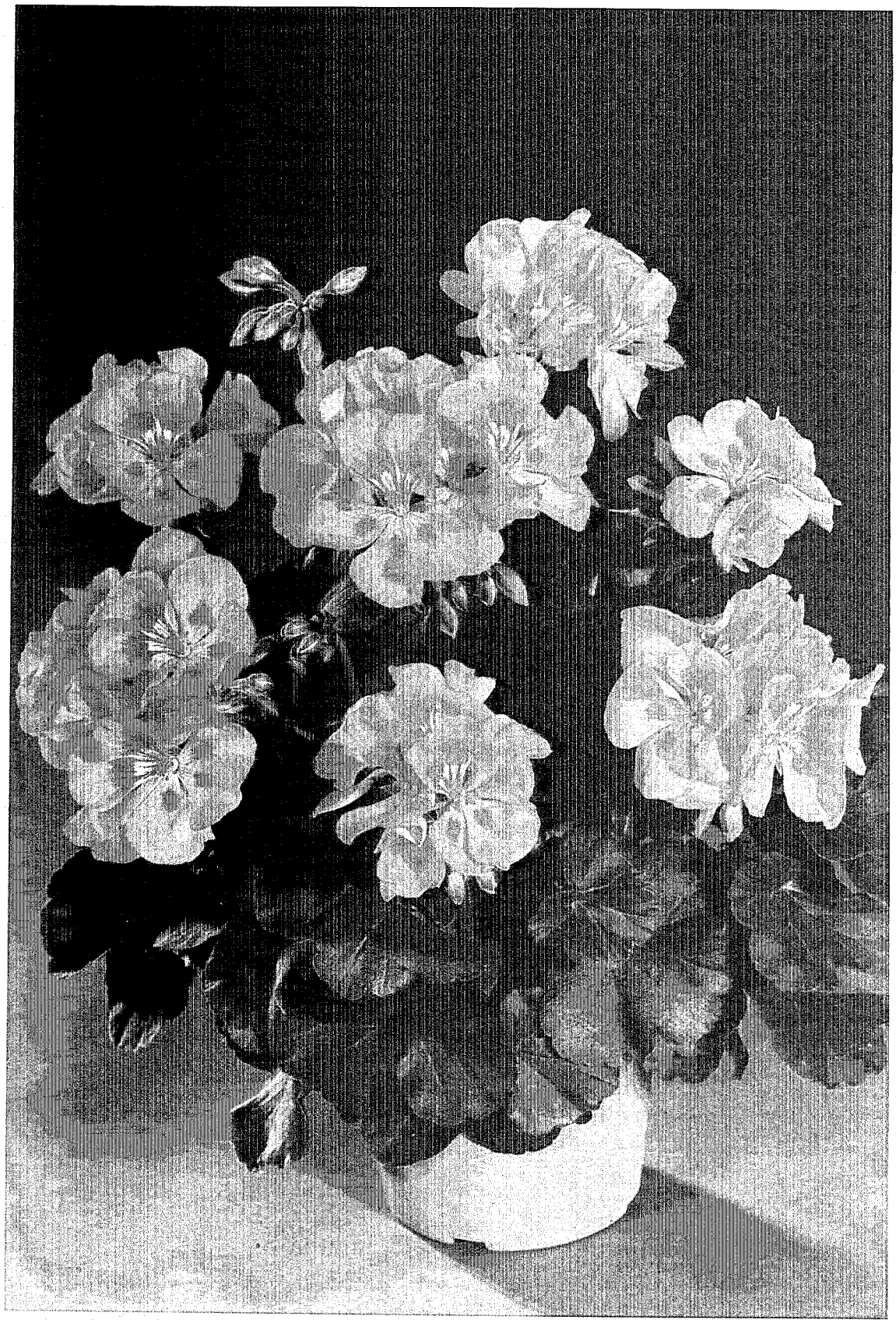

* * * * *